United States Patent [19]

Gilliland et al.

[11] Patent Number: 5,164,672

[45] Date of Patent: Nov. 17, 1992

[54] METHOD FOR MEASURING ELECTRICAL RESISTIVITY OF A CORE SAMPLE OF POROUS ROCK DURING WATER DRAINAGE AND IMBIBITION

[75] Inventors: Ron E. Gilliland, New Orleans, La.; Eve S. Sprunt, Farmers Branch, Tex.

[73] Assignee: Mobil Oil Corporation, Fairfax, Va.

[21] Appl. No.: 837,383

[22] Filed: Feb. 19, 1992

[51] Int. Cl.$^5$ .................... E21B 49/02; G01N 23/04; G01V 3/02

[52] U.S. Cl. .................... 324/376; 73/153; 250/255

[58] Field of Search .................. 324/376, 444; 73/152, 73/153; 250/255

[56] References Cited

U.S. PATENT DOCUMENTS

| | | | |
|---|---|---|---|
| 3,839,899 | 10/1974 | McMillen | 73/38 |
| 4,379,407 | 4/1983 | Masse et al. | 73/579 |
| 4,467,642 | 8/1984 | Givens | 73/152 |
| 4,546,318 | 10/1985 | Bowden | 324/376 |
| 4,649,483 | 3/1987 | Dixon | 364/422 |
| 4,686,477 | 8/1987 | Givens et al. | 324/366 |
| 4,799,382 | 1/1989 | Sprunt et al. | 73/153 |
| 4,868,751 | 9/1989 | Dogru et al. | 364/422 |
| 4,907,448 | 3/1990 | Givens | 73/153 |
| 4,926,128 | 5/1990 | Givens | 324/376 |

OTHER PUBLICATIONS

SCA Guidelines for Sample Preparation and Porosity Measurement of Electrical Resistivity Measurements by N. L. Maerefat et al., *The Log Analyst*, 1990, pp. 68-75.

Primary Examiner—Walter E. Snow
Attorney, Agent, or Firm—Alexander J. McKillop; Charles J. Speciale; George W. Hager, Jr.

[57] ABSTRACT

A two-phase fluid, flow having a first fluid and an immiscible second fluid, is passed through a core sample. The core sample is scanned with X-rays to produce a display of fluid distribution within the core sample. Electrical resistivity is measured along the length of the core sample for those intervals having uniform first fluid distribution. The two-phase flow is continued to repetitively decrease the first fluid saturation in a plurality of drainage cycles with electrical resistivity being again measured for each drainage cycle. Thereafter, the two-phase fluid flow is continued to repetitively increase the first fluid saturation in a plurality of imbibition cycles with electrical resistivity being again measured for each imbibition cycle.

11 Claims, 2 Drawing Sheets

METHOD FOR MEASURING ELECTRICAL RESISTIVITY OF A CORE SAMPLE OF POROUS ROCK DURING WATER DRAINAGE AND IMBIBITION

BACKGROUND OF THE INVENTION

This invention relates to the area of oil and natural gas exploration and, more particularly, to a method for identifying regions of rock formations having significant water saturations from which hydrocarbons may be produced without significant attendant water production.

Subsurface reservoirs of natural gas and petroleum, hereinafter referred to generically as "hydrocarbons" are typically found trapped in permeable geological strata beneath a layer of impermeable strata material. A hydrocarbon will "float" upon any ground water present, although typically a transition zone will exist between the two fluids due to the water being raised by capillary action of the permeable strata material. In some regions, impermeable layers may be relatively closely stacked atop one another trapping thin zones of what may be essentially hydrocarbons, essentially water or mixed hydrocarbons and water. A wellbore dropped through the formation and various layers may produce water if tapped in a transition region or mixed hydrocarbon and water zone. The cost of transporting, separating and disposing of the attendant water adds sufficiently to production costs that hydrocarbon reservoirs have often been left untapped where it is expected or believed they would produce an excessive amount of attendant water.

Water saturation present at various levels of a formation is typically determined from interpretation of conventional electrical (i.e. resistivity) logs taken through a borehole drilled through the formation. Water saturation of the available pore space of the formation is determined from the resistivity log measurements using the Archie equation set forth in "The Electrical Resistivity Log As An Aid In Determining Some Reservoir Characteristics", Trans. AIME, Vol. 46, pp. 54-62, 1942, by G. E. Archie. This equation is expressed as follows:

$$S_w{}^n = R_w/\phi^m R_t \qquad (1)$$

Where "$S_w$" is the fractional water saturation (i.e. free and bound water of the formation expressed as a percent of the available pore space of the formation), "$R_w$" is the formation water resistivity, "$\phi$" is the formation porosity, "$R_t$" is the formation resistivity indicated by the resistivity log, "n" is the saturation exponent and "m" is the porosity or cementation exponent. The Archie equation may be expressed in other ways and there are numerous methods in the art for determining, measuring or otherwise obtaining the various components needed to predict fractional water saturation $S_w$ from the log-indicated resistivity $R_t$, using the equation in any of its forms.

Archie defined two quantities that provided the basis for his water saturation equation (1). The first quantity is the formation factor F which defines the effect of the rock matrix on the resistivity of water as follows:

$$F = R_o/R_w \qquad (2)$$

where
$R_o$ = resistivity of water-saturated rock and
$R_w$ = water resistivity.

Archie reasoned that for a given value of $R_w$, the formation factor F would decrease with increasing porosity, $\phi$, to some exponent m:

$$F = 1/\phi^m \qquad (3)$$

This porosity exponent m has also become known as the cementation exponent. Thus Archie provided a useful characterization of a rock fully saturated with a conducting brine in terms of the water resistivity Rw, porosity $\phi$ and a rock parameter m. It is important to note that Archie assumed all conductance to be in the brine.

The second quantity is the resistivity index I defined as the ratio of the resistivity of a rock partially saturated with water and hydrocarbon $R_t$, to the same rock saturated fully with water, $R_o$, as follows:

$$I = R_t R_o \qquad (4)$$

Archie reasoned that as the water saturation decreased (i.e. hydrocarbon saturation increased) the resistivity $R_t$ and hence I would increase to some exponent n:

$$I = 1/S_w{}^n \qquad (5)$$

where $S_w$ = volume of water in pores/total volume. This exponent n has become known as the saturation exponent. It is again important to note that Archie assumed all conductance to be in the brine and further that all pores within the rock have the same water saturation $S_w$.

It is these two equations (3) and (5) for the formation factor F and resistivity index I respectively that Archie combined to provide the water saturation expression $S_w$ of equation (1). Certain logs provide porosity $\phi$, water samples provide the best values for $R_w$, and the cementation exponent m and saturation exponent n are obtained by electrical measurements on core samples.

Standard practice is to measure rock sample resistivities $R_o$ and $R_t$ for a number of water saturations and to plot the logarithm of I versus the logarithm of $S_w$. Such a logarithmic plot is a straight line with slope of $-n$. This plot, however, assumes that all rock pores are desaturated equally, all resistivities for partial water saturation are measured under uniform fluid distribution conditions throughout the rock sample, and all conductance is in the brine. If uniform fluid distribution has not been reached throughout the rock sample, then the value of the measured resistivity index I will not be correct and therefore the value of the saturation exponent n will not be the value of n that is characteristic of the rock. It is therefore the specific objective of the present invention to provide a method for measuring electrical resistivity of a rock sample that will yield a correct value for the saturation exponent n even under conditions in which water saturation has not reached uniform fluid distribution throughout the rock sample. Present methods cannot make such an identification, but merely rely on waiting periods after each new partial water saturation is effected in the rock sample over which it is assumed that uniform fluid distribution has been reached so that a resistivity measurement can be made.

SUMMARY OF THE INVENTION

In accordance with the present invention, a method is provided for measuring electrical resistivity of a core sample of porous rock during both fluid drainage and imbibition. A two-phase fluid flow having a first fluid and an immiscible second fluid is passed through a core sample. The core sample is scanned with X-rays to produce a display of fluid distribution along the length of the core sample. Electrical resistivity is measured along the length of the core sample wherein the display indicates the first fluid to be in uniform distribution. The two-phase fluid flow is continued to repetitively decrease first fluid saturation in a plurality of drainage cycles, with electrical resistivity being again measured for each such drainage cycle. Thereafter, the two-phase fluid flow is continued to repetitively increase first fluid saturation in a plurality of imbibition cycles with electrical resistivity being again measured for each such imbibition cycle. There is therefore produced a record of core sample electrical resistivity taken along the core sample in those intervals having uniform first fluid distribution during both drainage and imbibition of water within the core sample.

In a more specific aspect, the core sample is initially fully saturated with the first fluid. The core sample is scanned with X-rays to produce a display of the X-ray attenuation pattern within the core sample. These X-ray scans on the sample fully saturated with the first fluid are used along with X-ray scans of the sample fully saturated with the second fluid to determine fluid saturation at intermediate saturations. Electrical resistivity is measured along those lengths of the core sample having uniform fluid distribution as fully saturated with the first fluid. Following completion of the drainage and imbibition cycles, the sample is cleaned and fully resaturated with the second fluid. The core sample is scanned with X-rays to produce a display of the X-ray attenuation pattern. Preferably the first fluid is water, such as brine, and the second immiscible fluid is a hydrocarbon, such as an oil.

DESCRIPTION OF THE PREFERRED EMBODIMENT

Figure 1:
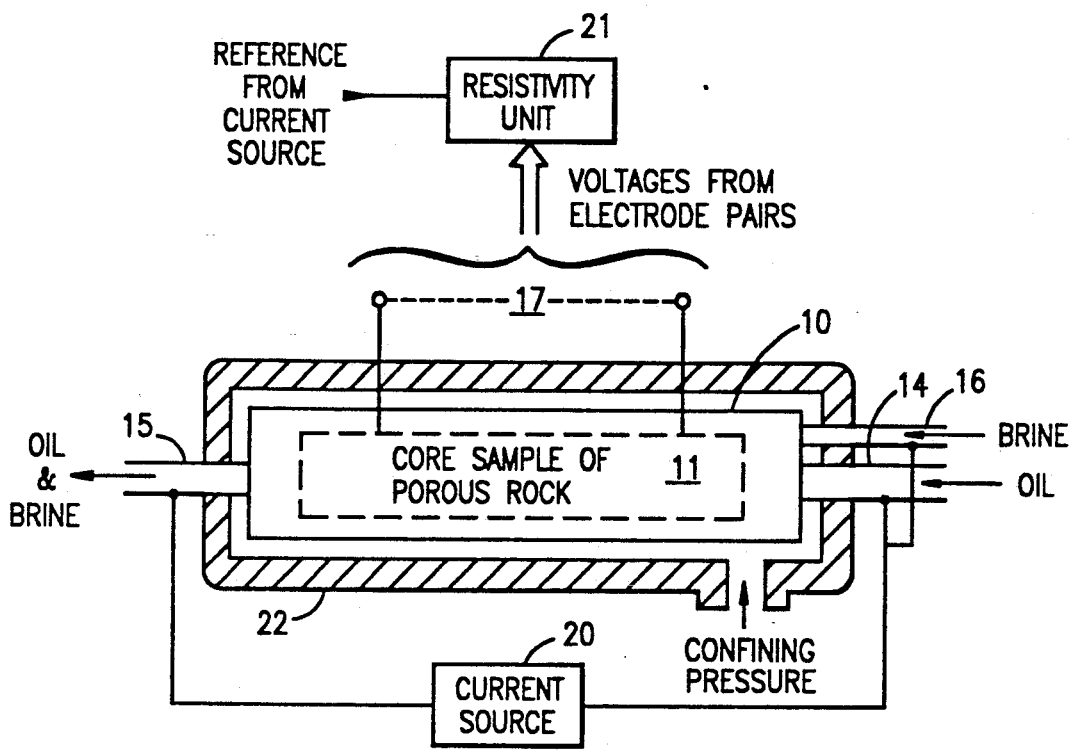
FIG. 1 illustrates apparatus in which a core sample may be placed for the carrying out of electrical resistivity measurements along the length of the core sample in accordance with the present invention.

The method of the present invention of making electrical resistivity measurements on a core sample during water drainage and imbibition may preferably be carried out with the apparatus shown in FIG. 1. A pressure sleeve 10, preferably natural or synthetic rubber, is in the form of a cylinder surrounding a core sample 11 of a porous rock to be measured for resistivity at a plurality of fluid saturations. Sleeve 10 is placed inside a suitable pressure vessel 22 that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al, the teachings of which are incorporated herein by reference. Through such a pressure vessel 22 a pressure is applied to the sleeve 10 and hence to the porous rock 11. Fluid inlets 14 and 16 and a fluid outlet 15 communicate with the sleeve 10. Both inlets 14 and 16 and outlet 15 also serve as current-conducting electrodes for passing current from a source 20 through the porous rock 11 when it contains a sufficient amount of electrically conducting fluid. A plurality of voltage electrodes 17 penetrate sleeve 10 and make contact with the porous rock at a plurality of spaced locations along the length of the porous rock.

In carrying out the method of the present invention with such apparatus of FIG. 1, a core sample of a porous rock 11 is initially fully saturated, by way of example, with an electrically conducting fluid, such as salt water, preferably brine, and placed within sleeve 10 under confining pressure. A current is passed through the porous rock at this initial saturation condition and the voltage $V_s$ along the length $L_s$ of the porous rock is measured between electrodes 17. As noted above, the inlets 14 and 16 and the outlet 15 function as current electrodes conducting current into and out of porous rock while the brine acts as the conducting medium within the porous rock and the porous member 13. Such voltage measurements, as well as later voltage measurements described below, may be carried out in accordance with the teachings of U.S. Pat. No. 4,467,642 to Givens, U.S. Pat. No. 4,546,318 to Bowden, U.S. Pat. No. 4,686,477 to Givens et al., U.S. Pat. No. 4,907,448 to Givens, and U.S. Pat. No. 4,926,128 to Givens, the teachings of which are incorporated herein by reference. From this voltage $V_s$ the resistance $r_s$ of the porous rock along the length $L_s$ is determined using Ohm's Law by the resistance section of the resistivity unit 21. The resistivity unit 21 calculates the resistivity $R_s$ using the resistance $r_s$, the length $L_s$ and the cross-sectional area of the core $A_c$ (note $R_s = r_s A_c / L_s$).

Typically, as described in "SCA Guidelines For Sample Preparation and Porosity Measurement of Electrical Resistivity Measurements" by N. L. Maerefat et al, *The Log Analyst*, March-April, 1990, pp. 68-75, electrical resistivity measurements on core samples are performed as the water saturation within the core sample is progressively decreased. However, in oil field situations, electric logs may be run in formations in which the water saturation is increasing, for example, a formation under water flooding. The electrical resistivity of a partially saturated core sample depends on the location of the water as well as the water saturation. Thus, whether the electrical measurement is performed during increasing or decreasing water saturation can make an important difference on the ultimate determination of the saturation exponent.

It is therefore a specific feature of the present invention to measure electrical resistivity of a core sample under a two-phase flow condition that alters the water saturation within the core sample with both decreasing (i.e. drainage) and increasing (i.e. imbibition) water saturations. Such a two-phase flow is provided by oil flow through inlet 14 and simultaneous brine flow through inlet 16 of sleeve 10. A typical alternating increasing and decreasing water saturation pattern may be effected by altering the water-to-oil flow ratio as follows:

| Measurement Number | Flow Ratio ($Q_W/Q_O$) | Direction of Change of Water Saturation |
|---|---|---|
| 1 | 1:0 | water baseline |

-continued

| Measurement Number | Flow Ratio ($Q_W/Q_O$) | Direction of Change of Water Saturation |
| --- | --- | --- |
| 2 | 10:1 | decreasing |
| 3 | 1:1 | decreasing |
| 4 | 1:10 | decreasing |
| 5 | 0:1 | decreasing |
| 6 | 1:10 | increasing |
| 7 | 1:1 | increasing |
| 8 | 10:1 | increasing |
| 9 | 1:0 | increasing |
| 10 | 10:1 | decreasing |
| 11 | 1:1 | decreasing |
| 12 | 1:10 | decreasing |
| 13 | 0:1 | decreasing |

After initially fully saturating the core sample with water, or brine, this two-phase flow thus provides a simple way to alter the core sample water saturation with both increasing and decreasing water saturations.

However, the water saturation is not uniformly distributed along the length of the core sample, which is a necessary condition for accurate electrical resistivity measurements. It is, therefore, a specific feature of the present invention to determine which portions of the length of the core sample do have a uniform fluid distribution and to measure electrical resistivity for each water saturation along such uniformly distributed portions of the length of the core sample.

Figure 2:
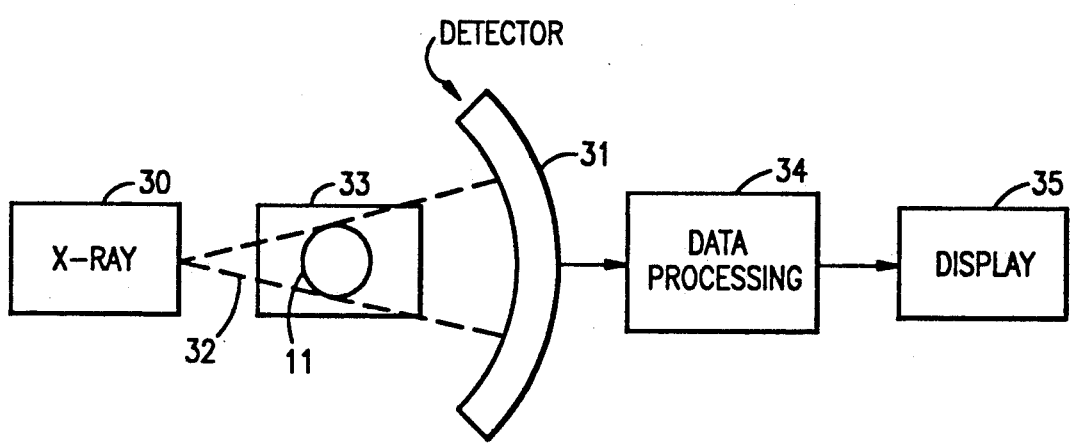
FIG. 2 is a pictorial view of a CT scanning system for use in scanning a core sample of a porous rock with X-rays in accordance with the method of the present invention.

Accordingly, the present invention provides for X-ray radiation of the saturated core sample to identify the portion of the length of the core sample over which the water saturation is uniformly distributed. More particularly, either computed tomography (CT) scanning, digital projection radiography or simple radiography may be used. In a preferred embodiment, a CT scanning system as illustrated in FIG. 2 may be employed for carrying out the X-ray measurements on the core sample. Such a CT scan produces a display or image of the density distribution in a cross-section or transverse slice of the core sample.

Referring now to FIG. 2, X-ray energy provided by the X-ray tube 30 passes through the core sample 11 and falls on the detector array 31. Rotation and indexing of core sample 11 within the X-ray fan beam 32 is provided by the gantry 33. The output of detector array 31 is passed through the data processing unit 34 to the display unit 35. After a desired number of scans are completed for a sample slice, the sample is indexed one slice width through the X-ray fan beam to place the next adjacent sample slice within the path of the X-ray fan beam. In this manner, a 3-D tomographic presentation can be made of the entire sample by compositing the cross-sectional views of each of the scan slices. Such a CT scanning system, while not forming a part of the present invention, is used in accordance with the method of the present invention to determine water distribution along the length of the core sample for both increasing and decreasing saturations. For a more detailed description of a CT scanning system which may be utilized in the method of the present invention, reference may be made to U.S. Pat. No. 4,649,483 to Dixon, U.S. Pat. No. 4,799,382 to Sprunt et al., and U.S. Pat. No. 4,868,751 to Dogru et al., the teachings of which are incorporated herein by reference.

Briefly, however, the resulting CT images of display 35 provide fluid saturation information exclusive of porous media effects. Such images are, in effect, two-dimensional maps of "CT number". The computed tomographic number ($N_{CT}$) is a numerical measure of the X-ray absorption properties of the sample of material being scanned by the X-ray fan beam and is routinely provided by the CT scanning system. Such a CT number is defined as:

$$N_{CT} = (\mu_m - \mu_w)/\mu_w \times 1000 \quad (1)$$

where $\mu$ = X-ray mass attenuation coefficient
m = material scanned, and
w = water.

Figure 3:
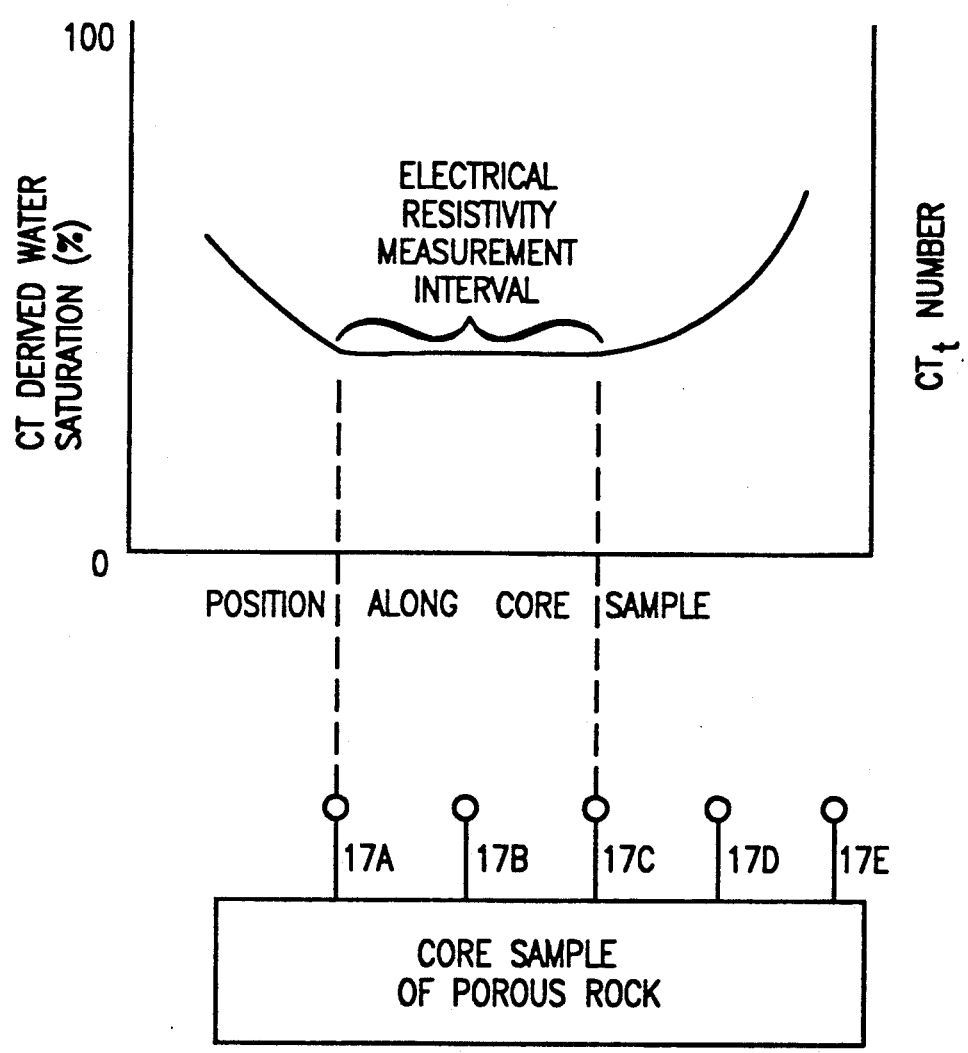
FIG. 3 illustrates a typical water saturation distribution curve along the length of a core sample being measured in accordance with the present invention for electrical resistivity to the apparatus of FIG. 1.

The scanned CT numbers are converted to water saturations along the length of the core sample as shown on the right vertical axis of FIG. 3 using baseline scans at two known saturations, such as 100% brine saturation and 100% oil saturation. Water saturation is calculated from the X-ray attenuation data as follows:

$$S_w = (CT_t - CT_o)/(CT_w - CT_o) \quad (2)$$

where $S_w$ = water saturation
$CT_o$ = oil CT number
$CT_w$ = water CT number, and
$CT_t$ = total two-phase CT number.

The oil or brine would typically contain an X-ray dopant to enhance the X-ray contrast between the oil and water.

Using the example of FIG. 3, water saturation is uniformly distributed along the interval of the core sample between electrodes 17A and 17C. Accordingly, resistivity measurements are made in accordance with the present invention across those electrodes 17 of FIG. 1 which span the core sample interval identified as having uniform fluid distribution.

Having now described and illustrated a preferred embodiment of the present invention, it is to be understood that various modifications and alterations may be made without departing from the spirit and scope of the invention as set forth in the appended claims.

We claim:

1. A method for determining electrical resistivity of a core sample of a porous rock during fluid drainage and imbibition, comprising the steps of:
   a) effecting a two-phase fluid flow through said core sample, a first fluid of said two-phase fluid flow being immiscible with a second fluid of said two-phase fluid flow,
   b) scanning said core sample with X-rays to produce a display of fluid distribution along the length of the core sample,
   c) determining from said display an interval along the length of the core sample wherein said first fluid is in uniform distribution,
   d) measuring electrical resistivity along the determined interval of core sample length wherein said first fluid is in uniform distribution,
   e) repeating steps a)–d) by decreasing the first fluid-to-second fluid flow ratio of said two-phase fluid flow to effect electrical resistivity measurements during a plurality of first fluid drainage cycles within the core sample, and
   f) repeating steps a)–d) by increasing the first fluid-to-second fluid flow ratio of said two-phase fluid flow to effect electrical resistivity measurements during a plurality of first fluid imbibition cycles within the core sample.

2. The method of claim 1 further including the steps of:
a) initially fully saturating said core sample with said first fluid,
b) scanning said core sample with X-rays to produce a display of the fully saturated core sample,
c) determining from said display the pattern of X-ray attenuation within the core sample fully saturated with said first fluid, and
d) measuring electrical resistivity within the fully saturated core sample.

3. The method of claim 1 further including the steps of:
a) cleaning and resaturating the sample with the second fluid following completion of the drainage and imbibition cycles,
b) scanning said core sample with X-rays to produce a display of the core sample fully saturated with the second fluid,
c) determining from said display the pattern of X-ray attenuation within the core sample fully saturated with said second fluid, and
d) using the X-ray attenuation pattern to determine fluid saturations during the drainage and imbibition cycles.

4. A method for determining electrical resistivity of a core sample of a porous rock during water drainage and imbibition comprising the steps of:
a) effecting a two-phase fluid flow of water and oil through said core sample,
b) scanning said core sample with X-rays to produce a display of the two-phase fluid saturation condition throughout the length of the core sample,
c) determining from said display intervals along the length of said core sample wherein said water is uniformly distributed,
d) measuring electrical resistivity along said determined intervals of the length of said core sample wherein said water is uniformly distributed,
e) repeating steps a)-d) by decreasing the water-to-oil flow ratio of said two-phase fluid flow, and
f) repeating steps a)-d) by increasing the water-to-oil flow ratio of said two-phase fluid flow thereby producing a record of core sample electrical resistivity during drainage and imbibition of water within said core sample.

5. The method of claim 4 further comprising the steps of:
a) initially fully saturating said core sample with water,
b) scanning said core sample with X-rays to produce a display of the fully water-saturated core sample,
c) determining from said display intervals along the length of the core sample the pattern of X-ray attenuation within the core sample fully saturated with water, and
d) measuring electrical resistivity of the fully water-saturated core sample.

6. A method for determining electrical resistivity of a core sample of a porous rock under varying fluid saturation conditions comprising the steps of:
a) saturating said core sample by effecting a flow of a first fluid through said core sample,
b) scanning said first fluid saturated core sample with X-rays to produce a display of the pattern of X-ray attenuation along the length of said core sample,
c) measuring electrical resistivity across selected intervals along the length of said core sample which is fully saturated with said first fluid,
d) effecting a second fluid flow through said core sample to decrease the first fluid saturation condition within the core sample and repeating step b), said second fluid flow being comprised of a two-phase fluid including said first fluid and an immiscible second fluid,
e) measuring electrical resistivity across selected intervals along the length of said core sample wherein said first fluid is identified from the X-ray attenuation pattern as being uniformly distributed, and
f) repeating steps d)-e) repetitively for a plurality of progressively decreasing first fluid saturation conditions within said core sample.

7. The method of claim 6 further comprising the steps of:
g) effecting a second fluid flow through said core sample to increase the first fluid saturation condition within the core sample and repeating step b),
h) measuring electrical resistivity across selected intervals along the length of said core sample wherein said first fluid is identified from the X-ray attenuation pattern as being uniformly distributed, and
i) repeating steps g)-h) repetitively for a plurality of progressively increasing first fluid saturation conditions.

8. The method of claim 6 wherein said first fluid comprises water and said second immiscible fluid comprises a hydrocarbon.

9. The method of claim 6 wherein said water is a brine and said second immiscible fluid is an oil.

10. A method for determining electrical resistivity of a core sample of a porous rock under conditions of both drainage and imbibition, comprising the steps of:
a) fully saturating a core sample with a first fluid,
b) scanning said core sample with X-rays to produce a display of X-ray attenuation along the length of said core sample fully saturated with said first fluid,
c) measuring electrical resistivity across selected intervals along the length of said core sample,
d) flooding said core sample with a second two-phase fluid containing said first fluid and an immiscible fluid to decrease the first fluid saturation condition within said core sample by drainage of a portion of said first fluid from said core sample and repeating step b),
e) measuring electrical resistivity across selected intervals of said core sample wherein said first fluid is identified from the X-ray attenuation pattern as being uniformly distributed,
f) repeating steps d)-e) repetitively for a plurality of progressively decreasing first fluid saturation conditions, and
g) flooding said core sample with said second two-phase fluid to increase the first fluid saturation condition within said core sample by imbibition of a portion of said first fluid into said core sample and repeating step b),
h) measuring electrical resistivity across selected intervals of said core sample wherein said first fluid is identified from the X-ray attenuation pattern as being uniformly distributed, and
i) repeating steps g)-h) repetitively for a plurality of progressively increasing first fluid saturation conditions, thereby providing a record of core sample electrical resistivity during both drainage and imbibition of said first fluid within said core sample.

11. A method for determining electrical resistivity of a core sample of a porous rock under conditions of both water drainage and imbibition, comprising the steps of:
   a) positioning a plurality of electrodes along the length of a core sample of porous rock, spacings between said electrodes defining subsections along the length of said core sample,
   b) irradiating said core sample with X-rays from a source of X-rays sequentially disposed at different positions along the length of said core sample,
   c) employing detector means to collect X-ray radiation passing through said core sample,
   d) producing computed tomograph images of said sample from the X-ray radiation collected by said detector,
   e) determining from said X-ray images those intervals along the length of said core sample wherein there is uniform water distribution,
   f) passing a current flow through the length of said core sample,
   g) measuring voltage between those electrodes of subsections of said core sample having uniform water distribution,
   h) determining core sample resistivity along said subsections having uniform water distribution,
   i) saturating said core sample with a two-phase fluid containing water and oil to decrease the water saturation condition within said core sample and repeating steps b)–h),
   j) repeating step i) repetitively for a plurality of progressively decreasing water saturation conditions within said core sample, and
   k) repeating step i) repetitively for a plurality of progressively increasing water saturation conditions within said core sample, whereby there is provided a record of core sample electrical resistivity during both water drainage and imbibition of said core sample.

* * * * *